(12) United States Patent
Kuhlmann

(10) Patent No.: US 10,544,988 B2
(45) Date of Patent: Jan. 28, 2020

(54) SYSTEM AND METHOD FOR DRYING A HOSE OF A CPAP MACHINE

(71) Applicant: Richard Kuhlmann, Madison Heights, MI (US)

(72) Inventor: Richard Kuhlmann, Madison Heights, MI (US)

(73) Assignee: Richard Kuhlmann, Madison Heights, MI (US)

( * ) Notice: Subject to any disclaimer, the term of this patent is extended or adjusted under 35 U.S.C. 154(b) by 83 days.

(21) Appl. No.: 15/938,432

(22) Filed: Mar. 28, 2018

(65) Prior Publication Data
US 2019/0301798 A1    Oct. 3, 2019

(51) Int. Cl.
| F26B 5/14 | (2006.01) |
| F26B 5/16 | (2006.01) |
| A61M 16/08 | (2006.01) |
| B08B 9/027 | (2006.01) |

(52) U.S. Cl.
CPC ........... *F26B 5/16* (2013.01); *A61M 16/0875* (2013.01); *A61M 2209/082* (2013.01); *A61M 2209/10* (2013.01); *B08B 9/027* (2013.01)

(58) Field of Classification Search
CPC ...... F26B 5/16; A61M 2209/10; B08B 9/027; A46B 5/002; A46B 5/0025; A46B 5/0037; A46B 5/005; A46B 5/0058; A46B 5/0062; A46B 5/0066; A46B 2200/3013; A46B 2200/40; A46B 2200/405
USPC .......................... 34/397, 437–441, 104, 239
See application file for complete search history.

(56) References Cited

U.S. PATENT DOCUMENTS

| 5,279,048 A * | 1/1994 | Lawall ................... A45D 20/12 34/90 |
| 8,002,225 B1 * | 8/2011 | Malone .................. A47B 81/00 211/118 |

OTHER PUBLICATIONS

Homebrew.stackexchange.com, Methods for Cleaning and drying tubing, Mar. 16, 2013 (Year: 2013).*

* cited by examiner

*Primary Examiner* — John P McCormack
(74) *Attorney, Agent, or Firm* — Stephen T. Olson; Harness, Dickey & Pierce, P.L.C.

(57) ABSTRACT

A system for drying a hose of a CPAP machine includes an elongated member, a drying element, a coupling element and a mounting member. The elongated member includes a first end and a second end and is flexible along its length. The coupling element is carried at the first end of the elongated member and couples the drying element to the elongated member. The mounting member mounts the system to a door to suspend the hose during drying of an interior of the hose.

18 Claims, 4 Drawing Sheets

SYSTEM AND METHOD FOR DRYING A HOSE OF A CPAP MACHINE

FIELD

The present disclosure relates to a system and method for drying a hose of a CPAP machine.

BACKGROUND

This section provides background information related to the present disclosure which is not necessarily prior art.

Continuous positive airway pressure (CPAP) therapy is a common treatment for obstructive sleep apnea and other conditions. Obstructive sleep apnea may naturally occur during sleep when the upper airway becomes narrow as the muscles relax. This reduces oxygen in the blood and causes arousal from sleep. Use of CPAP machines is now widespread in intensive care units and at home for the treatment of sleep apnea at home. The CPAP machine delivers a stream of compressed air via a hose to face mask, thereby maintain the airway under air pressure to reduce or prevent apneas by allowing unobstructed breathing.

Daily cleaning of CPAP machines, including the hose, is recommended to avoid risk of infection or exposure to unwanted fungi or molds. The hose may be cleaned with hot water and soap, for example. After cleaning, a residual amount of water may stay within the hose.

It would be desirable to have a system for drying an interior of the hose of a CPAP machine in a cost effecting and simple manner.

SUMMARY

This section provides a general summary of the disclosure, and is not a comprehensive disclosure of its full scope or all of its features.

According to one particular aspect, the present teachings are directed to a system for drying the interior of a hose of a CPAP machine. The system includes an elongated member, a drying element, a coupling element and a mounting member. The elongated member includes a first end and a second end and is flexible along its length. The coupling element is carried at the first end of the elongated member and couples the drying element to the elongated member. The mounting member mounts the system to a door to suspend the hose during drying of the hose.

According to another particular aspect, the present teachings are directed to a method for drying an interior of a hose of a CPAP machine with the system described in the prior paragraph. The method includes securing the drying element to the coupling member and passing the second end of the elongated member through the hose. The method additionally includes coupling the hose to the mounting member. The method further includes mounting the mounting member to a door such that the hose hangs downwardly from the mounting member and drawing the elongated member and the drying member down through the hose to dry an interior of the hose.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 a side view of a represents a system for drying a hose of a CPAP machine according to the present teachings, the system shown operatively associated with a drying element.

Corresponding reference numerals indicate corresponding parts throughout the several views of the drawings.

DETAILED DESCRIPTION

An exemplary embodiment will now be described more fully with reference to the accompanying drawings.

Figure 1:
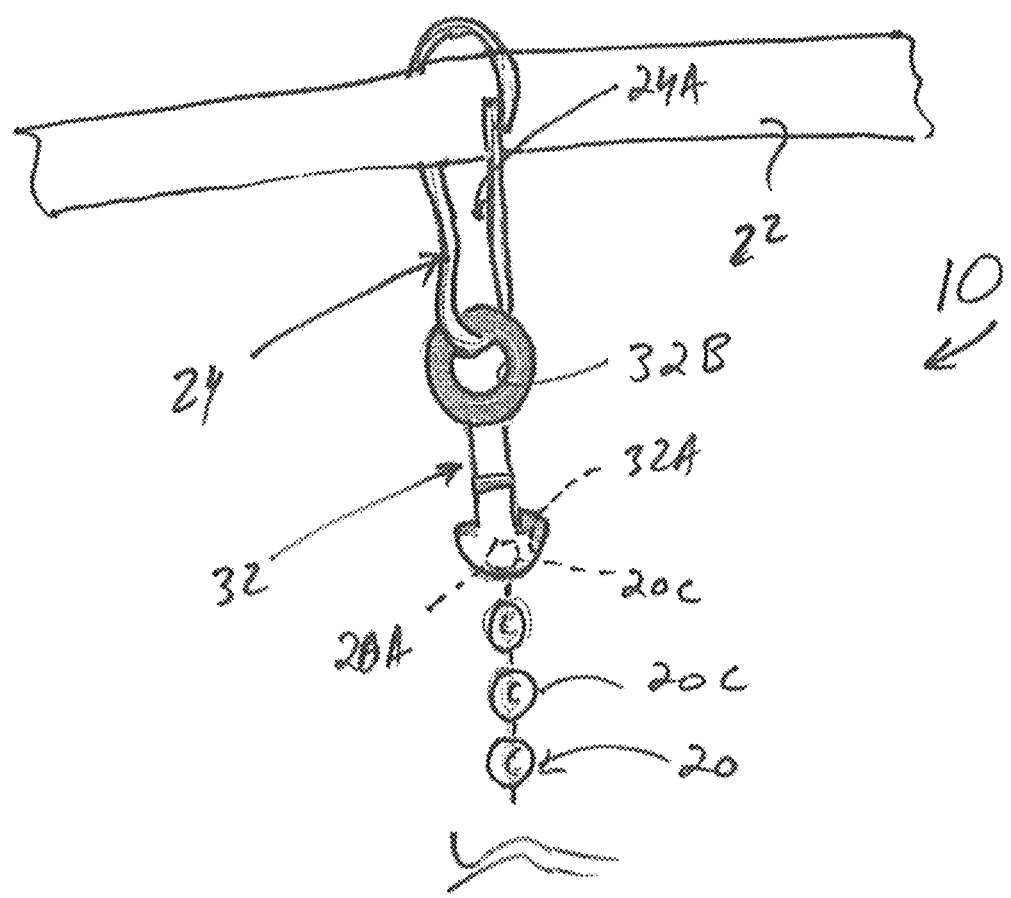
Figure 1:
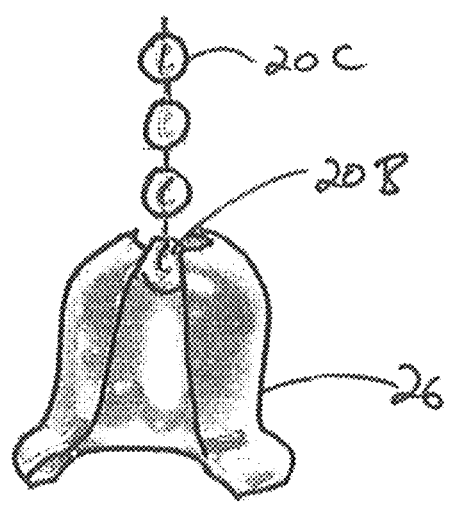
Figure 2:
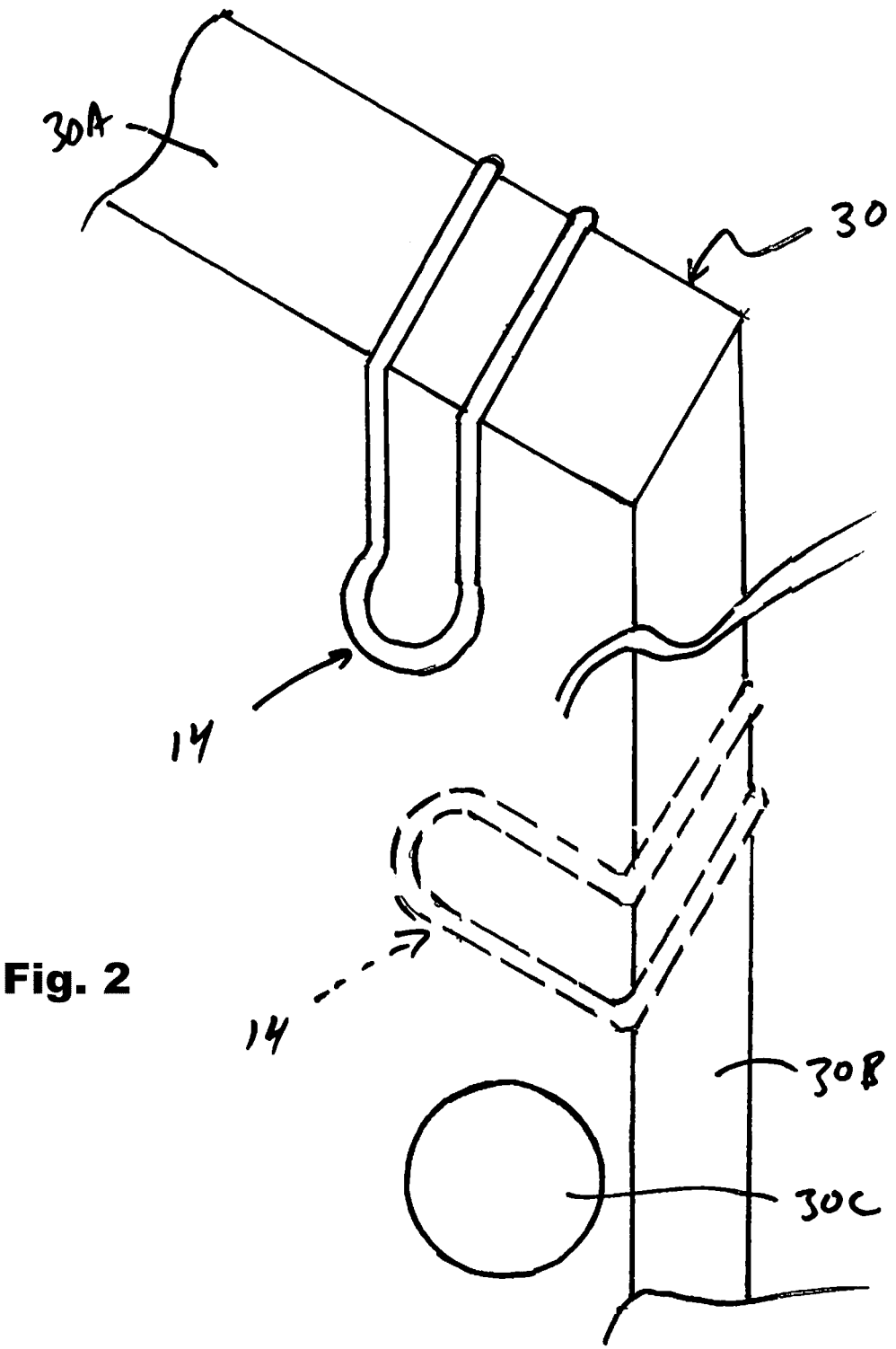
FIG. 2 is a perspective view of a mounting member of the system for drying a hose of a CPAP machine of FIG. 1 shown operatively attached to a door in a first position in solid lines and in a second, alternative position, in dashed lines.
Figures 3, 4:
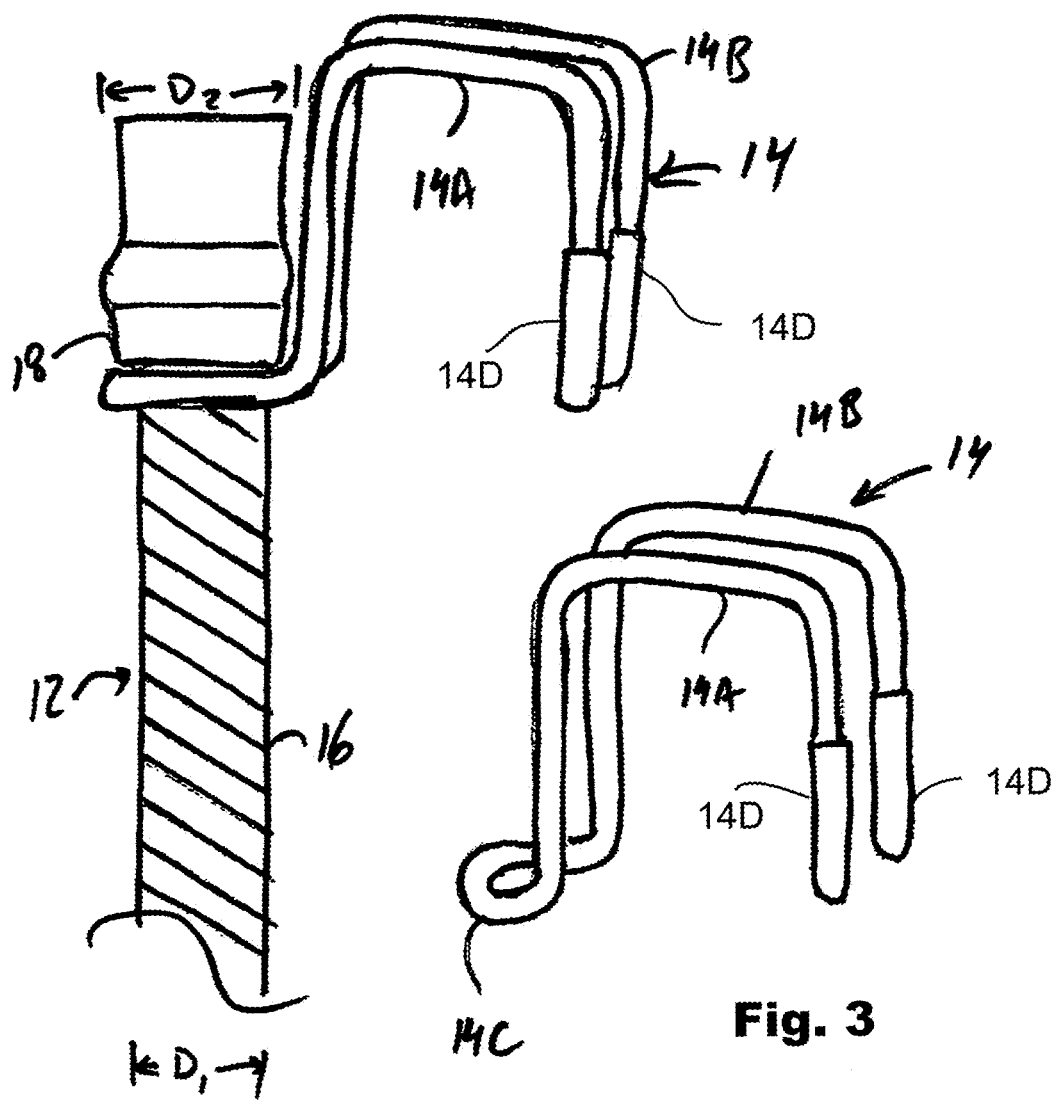
FIG. 3 is a perspective view of the mounting member of the system for drying a hose of a CPAP machine of FIG. 1.
FIG. 4 is another perspective view of the mounting member of the system for drying a hose of a CPAP machine of FIG. 1, the mounting member shown operatively associated with the hose of the CPAP machine.

With reference to FIGS. 1 through 4, a system for drying a hose of a CPAP machine is according to the present teachings is shown and generally identified at reference character 10. A CPAP hose 12 is shown in FIG. 4 operatively associated with a mounting member or mounting element 14 of the system 10. It will be understood that the hose 12 shown in the drawings is exemplary in construction and further understood that various other CPAP hoses may be used in connection with the system 10 of the present teachings. As illustrated, the CPAP hose 12 may conventionally include a main body portion 16 extending along a length that is flexible and has a first diameter $D_1$. The CPAP hose 12 may conventionally include an end 18 having an enlarged, second diameter $D_2$ that is greater than the first diameter $D_1$.

In addition to the mounting member 14, the system 10 for drying a hose 12 of a CPAP machine of the present invention is illustrated to generally include an elongated member 20, a drying element 22, and a coupling element 24. The elongated member 20 includes a first end 20A and a second end 20B and is flexible along its length. The coupling element 24 is carried at the first end 20A of the elongated member 20 and couples the drying element 22 to the elongated member 20. The system 10 may further include an end element or weight element 26 carried at the second end 20B of the flexible member 20. As will become further understood below, the mounting member 14 mounts the system 10 to a door 30 to suspend the hose 12 during drying of the hose 12.

In one particular application, the elongated member 20A may be a ball chain. The ball chain 20 may include a plurality of balls 20C. The elongated element 20 preferably has a length of at least 4 feet. The elongated element 20 more preferably has a length of at least 6 feet. In the particular application illustrated, the elongated element has a length of approximately 6 feet. It will be understood, however, that these lengths are exemplary and further that the present teachings may include an elongated element of differing dimensions or of a different construction.

The drying element 22 is constructed of an absorbent material. According to one particular application, the drying element 22 is a paper towel. For example, the drying element 22 may be constructed of a convention half sheet of paper towel. The half sheet may be cut in half and folded in any suitable pattern. The drying element 22 may be alternatively constructed of a sponge or other material capable of absorbing moisture or otherwise removing moisture from an interior of the hose 12.

The coupling element 24 may be a snap hook. As shown in FIG. 1, a central opening 24A of the coupling element 24 may receive the drying element 22. The coupling element 24 may be attached to the first end 20A of the elongated member 20 by a coupling 32. The coupling 32 may function to rotatably attach the coupling element 24 to the first end 20A of the elongated element 20 for rotation relative to the elongated element 20 about an elongated axis of the elongated element 20. In this regard, the coupling 32 may define a spherical recess 32A for receiving an uppermost ball 20C of the elongated element 20. An opposite end of the coupling 32 may define an opening 32B for receiving the snap hook 24.

The mounting member 14 may include first and second U-shaped portions 14A and 14B for releasably mounting to a door 30. The first and second U-shaped portions 14A and 14B may be parallel to one another. The mounting member 14 may further include a C-shaped portion 14C connecting the first and second U-shaped portions 14A and 14B. The free ends of the mounting member 14 may include rubber or plastic caps 14D to prevent scratching and to provide increased friction with the door 30 to further stabilize mounting. The C-shaped portion 14C may function to releasably engage the enlarged end 18 of the hose 12. In this regard, the C-shaped portion may have a radius of curvature that is greater than two times the first diameter $D_1$ of the hose and less than two times the second diameter $D_2$ of the enlarged end 18 of the hose 12. In the embodiment illustrated, the mounting member 14 unitarily formed to include the first and second U-shaped portions 14A and 14B and the C-shaped portion 14C.

With particular reference to FIG. 2, the mounting member 14 is shown attached to the door 30 in a first position in solid lines and in a second, alternative position, in dashed lines. In the first position, the mounting member 14 is attached to a top edge 30A of the door 30. In the second position, the mounting member 14 is attached to a side edge 30B of the door 30 above the door knob 30C.

Figure 5:
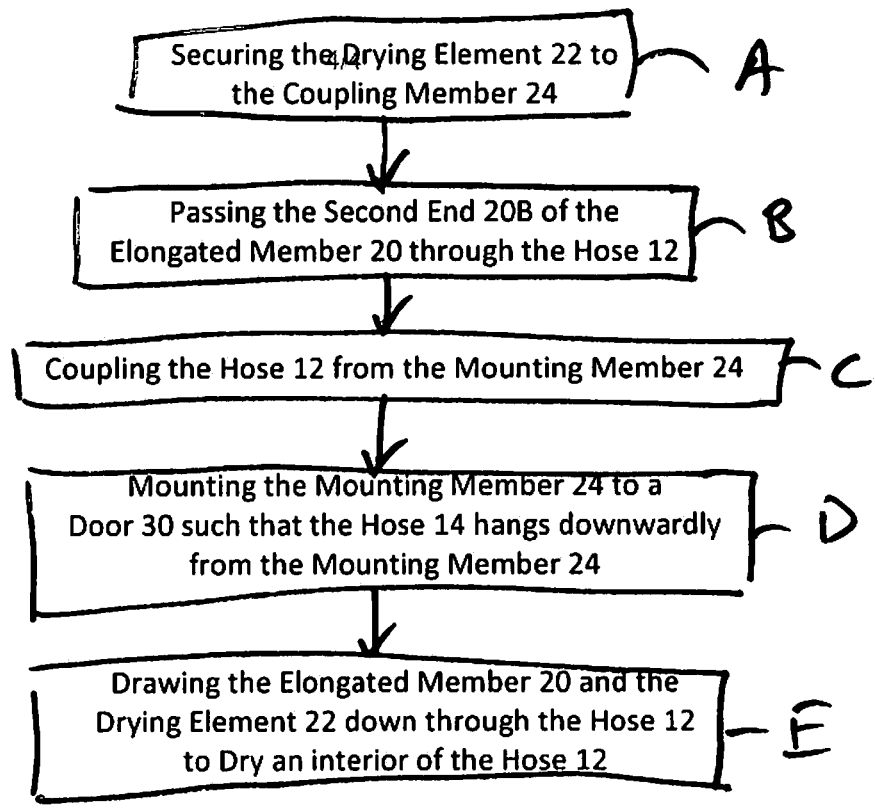
FIG. 5 illustrates the general steps of a method of the present teachings.

With additional reference to FIG. 5 and continued reference to FIGS. 1-4 of the drawings, an exemplary method of using the system 10 to dry the hose 12 of the CPAC machine will now be further described. It will be understood that the order of the steps as described herein may be altered within the scope of the present teachings.

In accordance with a first general step A, the drying element 22 is secured to the coupling member 24.

In accordance with a second general step B, the second end 20B of the elongated member 20 is passed through the hose 12.

In accordance with a third general step C, the mounting member 14 is coupled to the hose 12.

In accordance with a fourth general step D, the mounting member 14 is mounted to the door 30 such that the hose 12 hangs downwardly from the mounting member 14.

In accordance with a fifth general step E, the elongated member is drawn down through the hose 12 along with the drying element 22 to absorb or otherwise remove moisture from the interior of the hose 12.

The fourth and fifth general steps may be repeated as desired/necessary.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for drying an interior of a hose of a CPAP machine, the system comprising:
   an elongated member including a first end and a second end, the elongated member being flexible along a length thereof;
   a drying element;
   a coupling element carried at the first end of the elongated member, the coupling element coupling the drying element to the elongated member; and
   a mounting member for mounting the system to a door to suspend the hose during drying of the hose; and
   an end element carried at the second end of the elongated member.

2. The system for drying the interior of the hose of the CPAP machine of claim 1, wherein the end element is a weighted element.

3. The system for drying the interior of the hose of the CPAP machine of claim 1, wherein the elongated element has a length of at least 4 feet.

4. The system for drying the interior of the hose of the CPAP machine of claim 1, wherein the elongated element has a length of at least 6 feet.

5. A system for drying an interior of a hose of a CPAP machine, the system comprising:
   an elongated member including a first end and a second end, the elongated member being flexible along a length thereof;
   a drying element;
   a coupling element carried at the first end of the elongated member, the coupling element coupling the drying element to the elongated member; and
   a mounting member for mounting the system to a door to suspend the hose during drying of the hose;
   wherein the elongated element is a ball chain.

6. The system for drying the interior of the hose of the CPAP machine of claim 1, wherein the drying element is constructed of an absorbent material.

7. The system for drying the interior of the hose of the CPAP machine of claim 6, wherein the drying element is a paper towel.

8. The system for drying the interior of the hose of the CPAP machine of claim 1, wherein the coupling element is a snap hook.

9. A system for drying an interior of a hose of a CPAP machine, the system comprising:
   an elongated member including a first end and a second end, the elongated member being flexible along a length thereof;
   a drying element;
   a coupling element carried at the first end of the elongated member, the coupling element coupling the drying element to the elongated member; and
   a mounting member for mounting the system to a door to suspend the hose during drying of the hose;
   wherein the coupling element is rotatably attached to the first end of the elongated element for rotation relative to the elongated element about an elongated axis of the elongated element.

10. The system for drying the interior of the hose of the CPAP machine of claim 1, wherein the mounting member includes first and second U-shaped portions for releasably mounting to the door, the first and second U-shaped portions being parallel to one another.

11. The system for drying the interior of the hose of the CPAP machine of claim 10, wherein the mounting member further includes a C-shaped portion connecting the first and second U-shaped portions, the C-shaped portion for releasably engaging an enlarged end of the hose.

12. The system for drying the interior of the hose of the CPAP machine of claim 11, wherein the first U-shaped portion is in a first plane, the second U-shaped portion is in a second plane and the C-shaped portion is in a third plane, the third plane being perpendicular to the first and second planes.

13. The system for drying the interior of the hose of the CPAP machine of claim 11, wherein the mounting member unitarily formed to include the first and second U-shaped portions and the C-shaped portion.

14. The system for drying the interior of the hose of the CPAP machine of claim 11, in combination with the hose, the hose having a main body portion extending along the length that is flexible and has a first diameter and an end having an enlarged, second diameter greater than the first diameter.

15. A method for drying the interior of the hose of the CPAP machine with the system of claim 1, the method comprising:
   securing the drying element to the coupling member;
   passing the second end of the elongated member through the hose;
   coupling the hose to the mounting member;
   mounting the mounting member to the door such that the hose hangs downwardly from the mounting member; and
   drawing the elongated member and the drying element down through the hose to dry the interior of the hose.

16. The method for drying the interior of the hose of the CPAP machine of claim 15, further comprising repeating:
   passing the second end of the elongated member through the hose; and
   drawing the elongated member and the drying element down through the hose to dry the interior of the hose, as necessary to dry the interior of the hose.

17. The method for drying the interior of the hose of the CPAP machine of claim 15, wherein mounting the mounting member to the door includes mounting the mounting member to a top edge of the door.

18. The method for drying the interior of the hose of the CPAP machine of claim 15, wherein mounting the mounting member to the door includes mounting the mounting member to a side edge of the door.

* * * * *